United States Patent [19]

Arndt et al.

[11] Patent Number: 4,613,698

[45] Date of Patent: Sep. 23, 1986

[54] PROCESS FOR THE PREPARATION OF 6-CHLORO-2,4-DINITROANILINE

[75] Inventors: Otto Arndt, Hofheim am Taunus; Theodor Papenfuhs, Frankfurt am Main, both of Fed. Rep. of Germany

[73] Assignee: Hoechst Aktiengesellschaft, Fed. Rep. of Germany

[21] Appl. No.: 706,050

[22] Filed: Feb. 27, 1985

[30] Foreign Application Priority Data

Mar. 1, 1984 [DE] Fed. Rep. of Germany ....... 3407566
Mar. 9, 1984 [DE] Fed. Rep. of Germany ....... 3408631

[51] Int. Cl.$^4$ .............................................. C07C 85/24
[52] U.S. Cl. .................................... 564/412; 564/441; 260/694; 570/207; 570/209
[58] Field of Search ................ 564/412, 441; 260/694; 570/207, 209

[56] References Cited

FOREIGN PATENT DOCUMENTS 1587965 4/1981 United Kingdom .

OTHER PUBLICATIONS

Seyewetz, A. & Chaix, E. "Sur l'Oxydation à Froid des Matieres Colorantes en Milieu Acide, en Vue de Leur Décoloration par l'Hypochlorite de Soude" Bull. de la Société Chimique de France, Series 4, vol. 41 (1927) pp. 196–205.

*Primary Examiner*—Charles F. Warren
*Assistant Examiner*—John A. Sopp
*Attorney, Agent, or Firm*—Connolly and Hutz

[57] ABSTRACT

Process for the preparation of 6-chloro-2,4-dinitroaniline by chlorination of 2,4-dinitroaniline with sodium hypochlorite in water using acid, which comprises carrying out the chlorination in the presence of a mineral acid or strong organic acid at a pH value $\leq 0$ and in the presence of a dispersing agent at temperatures of about 40° to 50° C. and, when the chlorination has ended, either (a) filtering the resulting acid aqueous dispersion hot and washing the filtered reaction product with hot aqueous alkali solution, or (b) initially rendering the resulting acid aqueous dispersion alkaline with aqueous alkali solution and then filtering the mixture hot and subsequently washing the filtered reaction product with hot dilute mineral acid.

2 Claims, No Drawings

PROCESS FOR THE PREPARATION OF 6-CHLORO-2,4-DINITROANILINE

The present invention relates to an advantageous process for the preparation of 6-chloro-2,4-dinitroaniline by chlorination of 2,4-dinitroaniline by means of sodium hypochlorite (NaOCl), in which deficiencies of the known processes are avoided.

The preparation of 6-chloro-2,4-dinitroaniline by chlorination of 2,4-dinitroaniline is known per se by the following processes described in the literature:

(1) Chlorination of 2,4-dinitroaniline with elemental chlorine in water at 40°–50° C. in the presence of iron(III) chloride (IG Farben German Reichspatent No. 610,613 (1933), Friedländer 21, 310);

(2) Chlorination of 2,4-dinitroaniline with aqueous potassium chlorate solution mixed with hydrochloric acid (Versl.Akad. Amsterdam 31, 294, Chemisches Zentralblatt 1923 III, 746, and van de Vliet, Recueil des travaux chimiques des Pays-Bas, 43, 610);

(3) Chlorination of 2,4-dinitroaniline with elemental chlorine in glacial acetic acid and concentrated hydrochloric acid (Chattaway, Dowden, J. Chem. Soc. 125, 1196);

(4) Chlorination of 2,4-dinitroaniline with sodium hypochlorite (NaOCl) using 1 equivalent of hydrochloric acid at 15°–20° C. (Seyewitz, Chaix, Bulletin de la Societè Chimique de France (4), 41, 197, 204).

A 6-chloro-2,4-dinitroaniline which, from its much too low melting point of 145°–146° C., is highly contaminated (melting point of the pure product: 158° C.) is obtained by the last known process mentioned. In this known process, the successive sodium hydroxide liberated during the chlorination is neutralized by addition of a corresponding amount of hydrochloric acid.

According to Example 2 of German Patent Specification No. 610,613, the process described in the 1st literature reference requires finely ground 2,4-dinitroaniline and is characterized by a poor space/time yield (chlorination time: 15–20 hours).

The process described in the 2nd literature reference mentioned above leads to high pollution of the effluent with hydrochloric acid.

In the process described in the 3rd literature reference mentioned, regeneration of the acetic acid requires a relatively large additional technical effort.

It has been found that the deficiencies of the known processes (poor product quality, technical effort to be expended to achieve fine division of the starting substance, poor space/time yield, high pollution of the effluent by inorganic salts and technical effort to be expended for regeneration of the organic solvent used) can be avoided in the preparation of 6-chloro-2,4-dinitroaniline by chlorination of 2,4-dinitroaniline with sodium hypochlorite in water using acid by carrying out the chlorination in the presence of an excess of mineral acid or strong organic acids, based on the 2,4-dinitroaniline employed, and in particular at a pH value <0 and in the presence of a dispersing agent at temperatures of about 40° to 50° C., and, when the chlorination has ended, either (a) filtering the resulting acid aqueous suspension hot and washing the filtered reaction product with hot aqueous alkali solution, advantageously sodium carbonate solution, or (b) initially rendering the resulting acid aqueous suspension alkaline with aqueous alkali solution, advantageously sodium hydroxide solution, filtering the suspension hot and then washing the filtered reaction product with hot dilute mineral acid.

Possible mineral acids are, above all, the technical grade mineral acids, such as hydrochloric acid (30–38% strength), sulfuric acid, phosphoric acid or nitric acid, and examples of possible strong organic acids are formic acid or trichloroacetic acid. Hydrochloric acid (30–31% strength) is preferably employed, and in particular in an amount of 1.5–4 equivalents of HCl, based on the 2,4-dinitroaniline employed. However, it is also possible and particularly economical for the washing acid obtained, where appropriate, in the present process to be employed for establishing the pH value ≦ (in the sense of recycling).

As is known, chlorination of the aromatic hydrocarbon (ArH) by means of sodium hypochlorite takes place in accordance with the equation

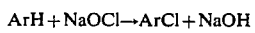

$$ArH + NaOCl \rightarrow ArCl + NaOH$$

According to the process, if, for example, only 1 equivalent of hydrochloric acid, based on the amount of 2,4-dinitroaniline employed, is used, which would just be sufficient to neutralize the 1 equivalent of NaOH formed, a deeply orange-colored suspension is obtained and the product isolated therefrom has a poor quality and yield. According to J. Chem. Soc. 123, 2791, azobenzenes partly result here, where appropriate via the N-chloro compounds, such as, for example, 6,6'-dichloro-2,4,2',4'-tetranitroazobenzene. In the course of our own investigations, 2,4-dinitrochlorobenzene and 1,2-dichloro-3,5-dinitrobenzene have also been found as by-products.

Due to the excess of acid used according to the invention (pH value of the reaction medium <0), contact between the 2,4-dinitroaniline to be chlorinated and hypochlorous acid (HOCl) above pH 0, which would be harmful, is also avoided.

Since the abovementioned known processes for the chlorination of 2,4-dinitroaniline to give 6-chloro-2,4-dinitroaniline have the serious disadvantages mentioned, and furthermore, in contradiction to the claim made in the 4th literature reference (Seyewitz, loc. cit.) that, apart from chlorination of the nucleus, no side reactions occur, our observations show that by-products are certainly formed and even traces of these have an adverse influence on the quality of the end product because of their strong color intensity, it must be considered surprising that 6-chloro-2,4-dinitroaniline can be prepared in a high yield and high purity by the process according to the invention, avoiding the disadvantages of the known processes.

The dispersing agent employed should fulfil the requirement of being relatively stable under the conditions of the chlorination according to the process. Examples of suitable dispersing agents are compounds from the group comprising alkylsulfonates, aralkylsulfonates (alkylbenzenesulfonates and alkylnaphthalenesulfonates), primary alkyl-sulfates (fatty alcohol sulfates, fatty alkyl-sulfates and fatty alcohol sulfonates), secondary alkyl-sulfates, fatty acid condensation products (condensates with substances containing amino groups, condensates with substances containing hydroxyl groups and condensates with aromatic hydrocarbons), polyglycol ethers and pyridine bases. As regards the amount to be employed, it is advantageous to use about 5–15 parts by weight of dispersing agent per mole of 2,4-dinitroaniline.

Further details and preferred embodiments of the process according to the invention are described below:

In preparation of the chlorination, the 2,4-dinitroaniline is stirred in 5-10 times the amount of water, with the addition of a dispersing agent, for example a secondary alkanesulfonate, which should fulfil the requirement of being relatively stable under the chlorination conditions. The acid, preferably 31% strength hydrochloric acid, is then allowed to run into the suspension. It would be inadvisable to use more than 4 equivalents of hydrochloric acid, because an increased pollution of the effluent would thereby be caused. In addition, side reactions in which the nitro and amino groups are replaced by chlorine increase as the acid concentration increases. The sodium hypochlorite (NaOCl) is used in the form of chlorine bleaching liquor. Chlorine bleaching liquor is understood as an aqueous solution of sodium hypochlorite and sodium chloride, which can be prepared by passing chlorine into cold aqueous sodium hydroxide solution (a 13.5 per cent strength by weight chlorine bleaching liquor contains 166 g of active chlorine per 1,229 g (=1 liter), corresponding to 2.34 moles of NaOCl per liter) (Gmelins Handbuch der anorg.Chemie (Gmelins Handbook of Inorganic Chemistry) 6 (1927), page 293; Ullmanns Encyklopädie der techn. Chemie (Ullmanns Encyclopedia of Industrial Chemistry) 9, 4th edition (1975), page 544).

It is advantageous to warm the suspension of the 2,4-dinitroaniline to temperatures of 40°-50° C. before the chlorination and to keep the reaction mixture at this temperature level during the chlorination. At lower temperatures, the hypochlorous acid would become more concentrated and start undesirable side reactions (orange colorations) or would dissociate more rapidly into oxygen and hydrochloric acid than it can usefully react. Temperatures above 50° C. are not advantageous because they promote dissociation of the hypochlorous acid and because of the risk of decomposition of the 6-chloro-2,4-dinitroaniline (safety reasons).

The sodium hypochlorite, which is metered in as chlorine bleaching liquor, should react with the 2,4-dinitroaniline as immediately as possible. A minimum temperature of about 40° C. is therefore required. For this purpose, it is also advantageous not to allow the chlorine bleaching liquor to run in too rapidly. Accumulation of the chlorine bleaching liquor during metering in to the reaction mixture is to be avoided, and this can be achieved by limiting the rate of dropwise addition of the chlorine bleaching liquor and by adequately stirring the reaction mixture during the dropwise addition of the chlorine bleaching liquor.

The optimum chlorination time is about 8 hours. Longer times are uneconomical because of the reduction in the space/time yield thereby caused. If the times are shorter than 4 hours, side reactions occur, these being easily recognizable by discoloration of the suspension to orange and darkening of the combined mother liquors and wash filtrates. If the optimum temperature, amount of acid and reaction time are obtained, complete conversion of the 2,4-dinitroaniline into 6-chloro-2,4-dinitroaniline is already achieved with sodium hypochlorite amounts of only a little more than 1 equivalent (for example 120 mole %, based on the 2,4-dinitroaniline). Under adverse conditions, even substantially larger excesses of sodium hypochlorite can be without benefit. It is advantageous to use the sodium hypochlorite in an amount of 1 to 1.5 equivalents, preferably 1.2 equivalents, based on the 2,4-dinitroaniline to be chlorinated.

It is furthermore advantageous initially to interrupt further addition of the chlorine bleaching liquor after an amount of chlorine bleaching liquor corresponding to one equivalent of sodium hypochlorite has been added and subsequently to stir the mixture for about 1-2 hours, while slowly increasing the temperature to 50° C. The remainder of the chlorine bleaching liquor (about 0.1-0.2 mole) is then allowed to run in, if appropriate after prior renewed addition of 1 equivalent of acid, for example 31% strength hydrochloric acid, and of dispersing agent. After the end of the conversion has been checked by thin layer chromatography, any residual active chlorine still present is destroyed with an equivalent amount of 40% strength sodium bisulfite liquor. The light yellow suspension is warmed to 60°-70° C. Warming serves only to prepare for the hot filtration.

The hot filtration is carried out at 70° C. This is followed by hot washing with water, 5% strength sodium carbonate solution and water again. The sodium carbonate runnings are first black-brown and then become light yellow, an indication that the highly colored secondary components are being effectively removed by the washing. Although the highly colored secondary components are very effectively removed from the reaction mixture in this process for isolating the 6-chloro-2,4-dinitroaniline, the formation of local "alkaline pockets" in the material on the filter cannot be excluded, and during any drying of the product, these lead to local decomposition sites, recognizable by the different color of solutions of samples taken from various points in the dried material (in, for example, dimethylformamide: either light orange-yellow or dark brown).

This disadvantage can be effectively excluded by bringing the hot suspension to pH 9 with concentrated sodium hydroxide solution before the hot filtration. Dark brown mother liquors are now obtained on filtration, but the product filtered off remains light-colored. The hot wash is then carried out with water (if approprate with the addition of dispersing agents), then with dilute mineral acid, for example 2% strength hydrochloric acid, and finally again with water. After drying at, for example, 60° C., the product no longer shows local decomposition sites. The filtration operations can be carried out on an open suction filter. There is no pollution by chlorine.

The 6-chloro-2,4-dinitroaniline is obtained in a high yield (95% of theory) and high purity (at least 98.5%), with a melting point of 156°-158° C.

Impurities contained in the product are: 2,4-dinitroaniline $\leq 1\%$, 2,6-dichloro-4-nitroaniline $\leq 0.5\%$, and 2,4-dinitrochlorobenzene $< 0.5\%$.

6-Chloro-2,4-dinitroaniline is a useful intermediate for dyestuffs, for example as a diazo component for a number of disperse dyestuffs (German Offenlegungsschrift No. 2,155,866, German Offenlegungsschrift No. 2,256,314, European Patent Application No. 0,064,221, European Patent Application No. 0,066,235, European Patent Application No. 0,073,414, Japanese Preliminary Published Application No. 72/33,481 and Japanese Preliminary Published Application No. 72/26,417).

The following examples serve to illustrate the process according to the invention without limiting it thereto. Parts denote parts by weight.

EXAMPLE 1

185 parts (1 mole) of 2,4-dinitroaniline in commercially available industrially moist form or industrially dry form are introduced at about 25° C., under the usual stirring conditions, into 1,000 parts of water to which 5 parts of a dispersing agent (secondary alkanesulfonate) have been added. 347 parts of 31% strength hydrochloric acid (3 moles) are allowed to run in. The suspension (pH <0) is then warmed to 40° C. A first portion of 565 parts of 13.5% strength chlorine bleaching liquor (corresponding to 1.07 moles of NaOCl=1.07 moles of active chlorine) is then added dropwise at 40° C. in the course of at least 4 and at most 6, preferably 4½–5, hours. The mixture is then warmed to 50° C. in the course of about 1 hour. 116 parts of 31% strength hydrochloric acid (1 mole) are then allowed to run in (pH ~0.5). If necessary, a further 2.5 parts of dispersing agent are added. The second portion of 70 parts of 13.5% strength chlorine bleaching liquor is subsequently added dropwise at 50° C. in the course of at least 1 and at most 3, preferably 2, hours. The mixture is then warmed to 60°–65° C. in the course of about 1 hour and, if necessary, a further 2.5 parts of dispersing agent are added. The thin, light yellow, fine-particled suspension is brought from pH 0.1 to pH 9.0 with 313 parts of 33% strength sodium hydroxide solution.

The suspension is then filtered at 70° C. on a suction filter, the mother liquor being dark brown. The material on the filter is subsequently washed successively with 1,000 parts of water of 70°–75° C., to which 2.5 parts of dispersing agent have been added, 2,000 parts of 0.2% strength hydrochloric acid at 70°–75° C. and 1,000 parts of water of 70°–75° C.

After drying at 60° C., 209 parts of 6-chloro-2,4-dinitroaniline with a purity of at least 98.5% and a melting point of 156°–158° C., corresponding to a yield of 95% of theory, are obtained as a purely yellow powder, the solution of which in dimethylformamide (100 mg/10 ml of DMF) is light orange-yellow.

The effluent (about 6,200 parts, pH 1.1) contains only about 9 parts of nitroaromatics and can be passed for biological purification after appropriate pretreatment.

If an equivalent amount of concentrated sulfuric acid or phosphoric acid is used instead of the hydrochloric acid, and the procedure is otherwise as described, virtually the same result is obtained.

EXAMPLE 2

The procedure is as described in Example 1, but without using dilute hydrochloric acid in the hot wash, i.e. under conditions of incomplete washing out of the alkali. A product which, after drying at 60° C., shows brownish decomposition in parts is obtained. Melting point: 150°–153° C.

EXAMPLE 3

The procedure is as described in Example 1, but with the difference that the suspension is filtered at pH 0.1. The mother liquor is light yellow-brown. The material on the suction filter is then washed successively with 1,000 parts of water at 70°–75° C. (if necessary with the addition of 2.5 parts of dispersing agent), 2,000 parts of 5% strength sodium carbonate solution at 70°–75° C. and 1,000 parts of water at 70°–75° C.

The filtrate runnings from the sodium carbonate wash are initially dark brown, and at the end light yellow. The same yield of product as according to Example 1 is obtained, the color of the solution of the moist product in dimethylformamide being light orange-yellow. After drying, the color of the solution is light orange-yellow or dark brown, depending on the point of sampling. The melting point is 150°–155° C.

EXAMPLE 4

The procedure is as described in Example 1, but using twice the amount of water during the chlorination. In addition, the first portion of 565 parts of chlorine bleaching liquor is added dropwise in the course of 8 hours (instead of in the course of about 5 hours). The second portion of 70 parts of chlorine bleaching liquor is added dropwise in the course of 2 hours.

Working up is as described in Example 3. After drying at 60° C., 207 parts of 6-chloro-2,4-dinitroaniline with a purity of 98.5% and a melting point of 154°–157° C. are obtained. The yield is 94% of theory. Both measures (dilution and prolonging of the chlorination time) lead to no improvement in the yield and quality in comparison with the procedure of Example 1, and only to a reduction in the space/time yield (=amount of space and time expended per unit quantity of end product).

EXAMPLE 5

The procedure is as described in Example 4, but with the difference that the suspension of the 2,4-dinitroaniline is subjected to wet grinding with a high performance dispersing apparatus before the chlorination. The same yield and quality as in the procedure of Example 4 are obtained.

EXAMPLE 6

The procedure is as in Example 5, but with the difference that the suspension of the 2,4-dinitroaniline is mixed with only 173 parts of 31% strength hydrochloric acid (1.5 moles), and in addition no further hydrochloric acid is added later. Furthermore, the chlorination is carried out with somewhat more chlorine bleaching liquor (=850 parts, corresponding to 1.6 moles of active chlorine).

Only 190 parts of 6-chloro-2,4-dinitroaniline with a melting point of 138°–140° C. are obtained. The thin layer chromatogram shows that the product is still considerably contaminated with 2,4-dinitroaniline. From this, it follows that in spite of the increased use of chlorine bleaching liquor, conversion under these conditions is incomplete. The product is not light yellow but light yellow-orange.

EXAMPLE 7

The procedure is as in Example 4, but with the difference that the first portion of chlorine bleaching liquor (=565 parts) is added dropwise in only 4 hours and the 2nd portion (=70 parts) is added dropwise in only 1 hour. After drying at 60° C., only 196 parts of 6-chloro-2,4-dinitroaniline of melting point 145°–155° C. are obtained.

The mother liquor is considerably darker in color than in Example 4.

EXAMPLE 8

(Comparison example without the addition of a dispersing agent)

The procedure is as described in Example 1, but with the difference that no dispersing agent is added throughout the entire course of the process. When the chlorination has ended, the suspension is considerably more coarse-particled than that obtained in the procedure of Example 1.

After hot filtration at pH 9, the usual wash (but without the use of a dispersing agent) and drying at 60° C., 197 parts of 6-chloro-2,4-dinitroaniline of melting point 141°–143° C. are obtained (containing 12.6% of 2,4-dinitroaniline). The resulting product is granular and non-uniformly colored (yellow with partial brownish discoloration).

We claim:

1. A process for the preparation of 6-chloro-2,4-dinitroaniline by chlorination of 2,4-dinitroaniline with sodium hypochlorite in water using acid, which comprises carrying out the chlorination in the presence of a mineral acid or strong organic acid at a pH value $\leq 0$ and in the presence of a dispersing agent at temperatures of about 40° to 50° C. and, when the chlorination has ended, either (a) filtering the resulting acid aqueous dispersion hot and washing the filtered reaction product with hot aqueous alkali solution, or (b) initially rendering the resulting acid aqueous dispersion alkaline with aqueous alkali solution and then filtering the mixture hot and subsequently washing the filtered reaction product with hot dilute mineral acid.

2. The process as claimed in claim 1, wherein the chlorination is carried out in the presence of 1.5 to 4 equivalents of hydrochloric acid (HCl), based on the 2,4-dinitroaniline employed.

* * * * *